United States Patent
Slattery, Jr. et al.

(10) Patent No.: US 9,662,258 B2
(45) Date of Patent: May 30, 2017

(54) PATIENT COLONOSCOPY ABDOMINAL COMPRESSION DEVICE AND METHOD

(71) Applicant: N.M. Beale Company, Inc., Harvard, MA (US)

(72) Inventors: James E. Slattery, Jr., Lynnfield, MA (US); Karen M. Slattery, Lynnfield, MA (US)

(73) Assignee: N.M. Beale Company, Inc., Harvard, MA (US)

( * ) Notice: Subject to any disclaimer, the term of this patent is extended or adjusted under 35 U.S.C. 154(b) by 674 days.

(21) Appl. No.: 13/898,800

(22) Filed: May 21, 2013

(65) Prior Publication Data

US 2014/0350341 A1 Nov. 27, 2014

(51) Int. Cl.
*A61B 1/00* (2006.01)
*A61G 13/12* (2006.01)
*A61B 1/31* (2006.01)

(52) U.S. Cl.
CPC .............. *A61G 13/123* (2013.01); *A61B 1/31* (2013.01)

(58) Field of Classification Search
CPC ....... A61B 1/31; A61B 1/00131; A61B 17/12; A61B 17/1325; A61B 5/0053; A61G 13/12; A61G 13/1205; A61G 13/121; A61G 13/1225; A61G 13/123; A61G 13/1235; A61G 13/124; A61G 13/1245; A61G 13/125; A61H 39/04
USPC .................... 606/201, 204; 602/53; 600/490; 128/845, 898; 5/648, 652, 655.9, 636, 5/637, 643
See application file for complete search history.

(56) References Cited

U.S. PATENT DOCUMENTS

| | | | | | |
|---|---|---|---|---|---|
| 1,934,918 A | * | 11/1933 | Everson | .................. | A61G 17/04 27/21.1 |
| 4,398,707 A | * | 8/1983 | Cloward | ................. | A61G 13/12 5/621 |
| 4,889,109 A | * | 12/1989 | Gifford | ................. | A47C 20/021 5/922 |
| 4,923,187 A | * | 5/1990 | Mombrinie | .......... | A61B 6/0442 5/601 |
| 5,154,477 A | * | 10/1992 | Lacy | ....................... | A47C 7/383 297/397 |
| 5,454,779 A | * | 10/1995 | Lurie | ...................... | A61H 31/00 601/43 |

(Continued)

FOREIGN PATENT DOCUMENTS

EP 0792130 B1 7/2000

OTHER PUBLICATIONS

Susan Drysdale, "The Incidence of Upper Extremity Injuries in Canadian Endoscopy Nurses", Gastroenterology Nursing, Society of Gastroenterology Nurses and Associates, vol. 34(1), Jan./Feb. 2011, p. 26-33.

(Continued)

*Primary Examiner* — Eric S Gibson
(74) *Attorney, Agent, or Firm* — Iandiorio Teska & Coleman, LLP

(57) ABSTRACT

A patient colonoscopy abdominal compression device and method. Spaced pressure columns are configured to press on the iliac. A palpation arch between the spaced pressure columns is configured to allow monitoring of scope movement and to insure loop control is correct and is also configured to transfer pressure from the patient or a nurse to the iliac via the pressure columns.

9 Claims, 4 Drawing Sheets

(56) References Cited

U.S. PATENT DOCUMENTS

| | | | | |
|---|---|---|---|---|
| 5,491,855 A * | 2/1996 | Charles | A47G 9/1009 | 5/636 |
| 5,664,271 A * | 9/1997 | Bellavance | A47C 20/025 | 5/630 |
| 5,685,321 A * | 11/1997 | Klingenstein | A61F 5/445 | 128/845 |
| 5,774,916 A * | 7/1998 | Kurhi | A61F 5/055 | 128/845 |
| D397,270 S * | 8/1998 | Maalouf | | 5/636 |
| 5,953,749 A * | 9/1999 | Backs | A47C 20/025 | 128/845 |
| 6,065,166 A * | 5/2000 | Sharrock | A61G 7/065 | 5/630 |
| 6,088,855 A * | 7/2000 | Connolly | A47C 7/383 | 297/397 |
| D438,046 S * | 2/2001 | Palm | | 5/630 |
| 6,299,248 B1 * | 10/2001 | Gennaro | A47C 7/425 | 297/219.1 |
| 6,331,349 B1 * | 12/2001 | Kalinoski | F16J 15/064 | 174/358 |
| 6,435,617 B1 * | 8/2002 | McNair | A47C 7/383 | 297/397 |
| 6,557,197 B1 * | 5/2003 | Graham | A47C 20/026 | 5/630 |
| 6,622,325 B1 * | 9/2003 | Garza | A47G 9/10 | 5/636 |
| 6,672,311 B2 | 1/2004 | Rindfleish | | |
| D543,214 S * | 5/2007 | Stewart | | D14/460 |
| D576,439 S * | 9/2008 | Yaroshenko | | D6/601 |
| 7,426,930 B1 * | 9/2008 | Bailey | A61G 7/05 | 128/112.1 |
| 7,806,471 B2 * | 10/2010 | Nishimoto | A47D 15/006 | 297/219.12 |
| 7,841,657 B2 * | 11/2010 | Nishimoto | A47D 15/006 | 297/219.1 |
| 7,958,582 B1 * | 6/2011 | Scamardo | A47C 7/383 | 297/392 |
| D661,191 S * | 6/2012 | Malone | | D9/456 |
| 8,584,285 B1 * | 11/2013 | Sipherd | A47C 7/383 | 5/636 |
| D697,739 S * | 1/2014 | Nabeta | | D6/601 |
| 2011/0016633 A1 * | 1/2011 | Eason | A47C 20/027 | 5/655.9 |
| 2011/0087263 A1 * | 4/2011 | Arber | A61B 17/135 | 606/202 |
| 2013/0178893 A1 * | 7/2013 | Hathorn | A61F 5/0009 | 606/201 |
| 2013/0254998 A1 * | 10/2013 | Walker | A47G 9/1081 | 5/637 |
| 2014/0350341 A1 * | 11/2014 | Slattery, Jr. | A61G 13/123 | 600/118 |

OTHER PUBLICATIONS

Prechel et al., "The Importance of Abdominal Pressure During Colonoscopy: Techniques to Assist the Physician and to Minimize Injury to the Patient and Assistant", The Society of Gastroenterology Nurses & Associates, vol. 28(3), May/Jun. 2005, p. 232-236.

* cited by examiner

PATIENT COLONOSCOPY ABDOMINAL COMPRESSION DEVICE AND METHOD

FIELD OF THE INVENTION

The invention relates to performing colonoscopies.

BACKGROUND OF THE INVENTION

During a colonoscopy, a nurse must control looping of a colonoscope advanced by the physician. The nurse presses on the patient's abdomen at suspected loop sites. See "The Importance of Abdominal Pressure during Colonoscopy: Techniques To Assist The Physician And To Minimize Injury To The Patient And Assistant," Gastroenterology Nursing, Vol. 28 (3), May/June 2005, p 232-236 incorporated herein by this reference.

As a result, musculoskeletal injuries are prevalent in endoscopy nurses. See Gastroenterology Nursing, Vol. 34, No. 1, January/February 2011 (p 26-33) also incorporated herein by this reference.

Those skilled in the art have attempted to make it easier to compress the patient's abdomen. For example, U.S. Pat. Nos. 5,685,321 and 6,672,311 and published U.S. Patent Application No. 2011/0087263 disclose bladders located in a worn garment. To our knowledge, none of these devices have been commercialized nor are they in wide spread use. European patent specification EP 0 792 130 B1 discloses a rubber ovoid shaped body with an anchoring protuberance used as a "straightener."

Despite such prior art, nurses continue to suffer musculoskeletal injuries.

SUMMARY OF THE INVENTION

In accordance with various aspects of the subject invention, in at least one embodiment, the invention presents a patent colonoscopy abdominal compression device and method including spaced pressure columns and a palpation arch.

Featured is a patient colonoscopy abdominal compression device comprising spaced pressure columns configured to press on the iliac. A palpation arch is between the spaced pressure columns and is configured to monitor scope movement and loop control and also configured to transfer pressure from the patient or a nurse to the iliac via the pressure columns. In one design, the two pressure columns are rectangular in cross section and the pressure columns are tapered. The arch may be curved and preferably includes a top flat surface with spaced edges for pivoting the device.

Also featured is a patient colonoscopy abdominal compression method comprising locating spaced pressure columns on a lateral patient's abdomen. The patient is rolled toward prone so at least one said pressure column applies pressure to a region of the abdomen. During the colonoscopy procedure, scope movement and loop control is monitored between the two spaced pressure columns. In one example, one said spaced pressure column is located adjacent the iliac. The method may further include adjusting the position of the spaced columns during the procedure. The method may also include adjusting the position of the patient during the procedure, for example, rolling the patient fully prone.

Also featured is a patient colonoscopy abdominal compression method comprising locating, on a patient's abdomen, spaced pressure columns connected by a bridge, applying pressure to the bridge so the pressure columns press on a different region of the abdomen for colonoscope loop control, and monitoring scope movement and loop control under the bridge.

In one example, pressure is applied by the patient laying on the spaced pressure columns and the bridge is adjacent a medical table. In another example, pressure is applied by a nurse pressing on the bridge.

The subject invention, however, in other embodiments, need not achieve all these objectives and the claims hereof should not be limited to structures or methods capable of achieving these objectives.

BRIEF DESCRIPTION OF THE SEVERAL VIEWS OF THE DRAWINGS

Other objects, features and advantages will occur to those skilled in the art from the following description of a preferred embodiment and the accompanying drawings, in which.

DETAILED DESCRIPTION OF THE INVENTION

Figure 1:
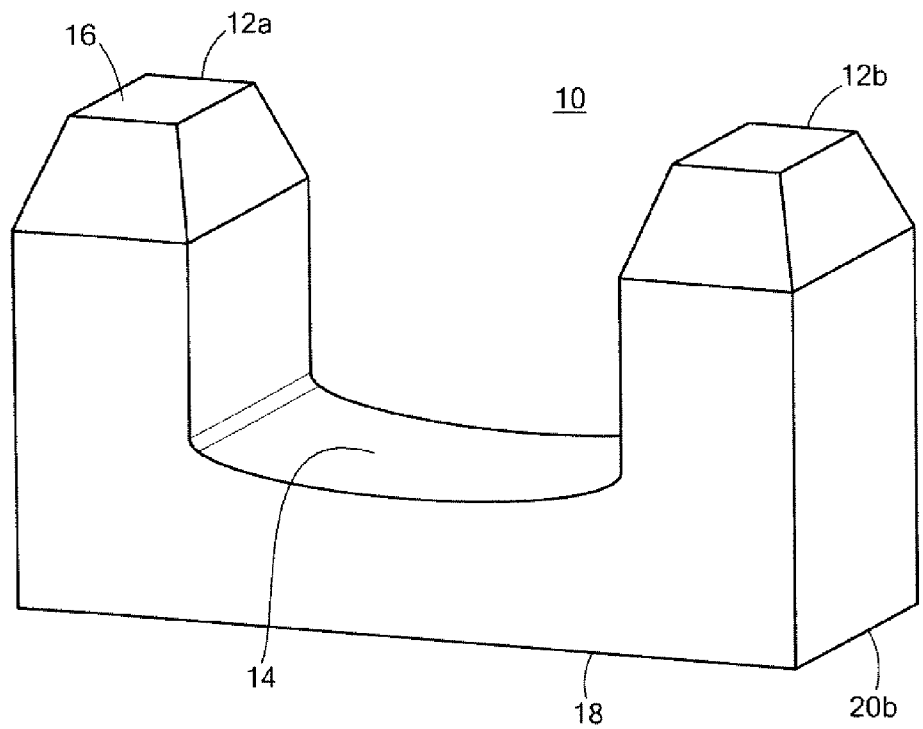
FIG. 1 is a schematic three dimensional front view of the top of an example of a patient colonoscopy abdominal compression device in accordance with the invention.

Aside from the preferred embodiment or embodiments disclosed below, this invention is capable of other embodiments and of being practiced or being carried out in various ways. Thus, it is to be understood that the invention is not limited in its application to the details of construction and the arrangements of components set forth in the following description or illustrated in the drawings. If only one embodiment is described herein, the claims hereof are not to be limited to that embodiment. Moreover, the claims hereof are not to be read restrictively unless there is clear and convincing evidence manifesting a certain exclusion, restriction, or disclaimer.

Figure 2:
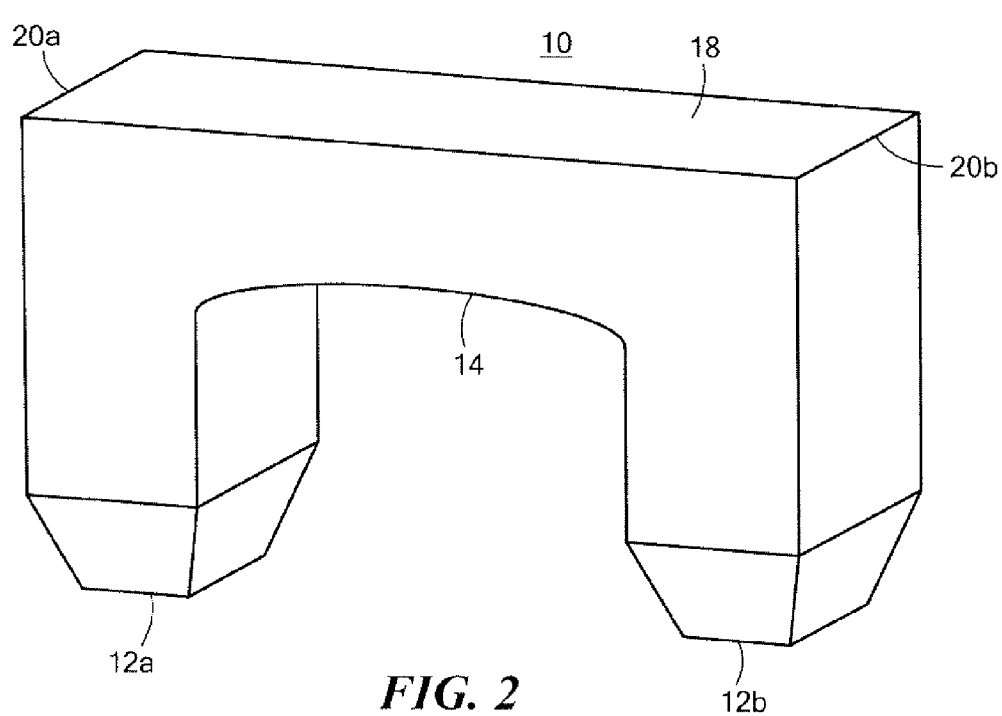
FIG. 2 is a schematic three dimensional front bottom view of the device of FIG. 1.

FIGS. 1-2 depict an example of a prototype example of a patient colonoscopy abdominal compression device 10 with spaced pressure column 12a and 12b configured to press on patient iliac regions and/or umbilical/epigastric regions. Palpation arch or bridge 14 (typically curved approximately 30°) between pressure columns 12a and 12b allows a nurse's hand to pass between the pressure columns and to touch/compress the abdomen to monitor scope movement and for loop control. Arch 14 is also configured to transfer pressure from a nurse or the patient himself to the pressure columns as discussed below.

Here, in this particular example, the pressure columns 12 and 12b are rectangular (e.g., square) in cross section and taper as shown. In one design, flat face area 16 is 1" by 1" and each pressure column is 5" long. Arch 14 is 2¾" thick by 2" wide. Flat arch face 18 is 8" long and 2" wide. Before the taper, each pressure column is 1½" wide and 1½" across.

Arch surface 18, FIG. 2 has spaced distal sharp corner edges 20a and 20b serving as fulcrum points for pivoting the device. Material used for the device 10 include a rigid closed cell foam or even hard plastic.

The design of device 10 allows for point specific compression of the abdomen representing a modified "open hand" technique. A foam body is used because it is light weight, not too compressible, and clean. Closed cell foam allows for transmission of movement of the colonoscope and the use of air for insufflation and suction enabling the assistant to monitor the progression of the colonoscope tip. The dimensions of one preferred device coincide with the dimensions of the average human pelvis, approximately 135 mm from iliac to iliac.

Figure 3:
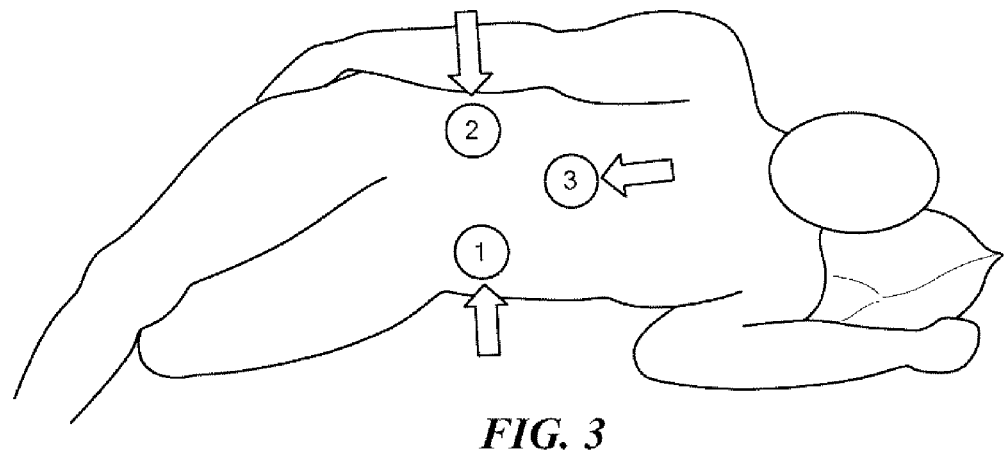
FIG. 3 is a view of a patient sedated and laying lateral on a hospital bed.
Figure 4:
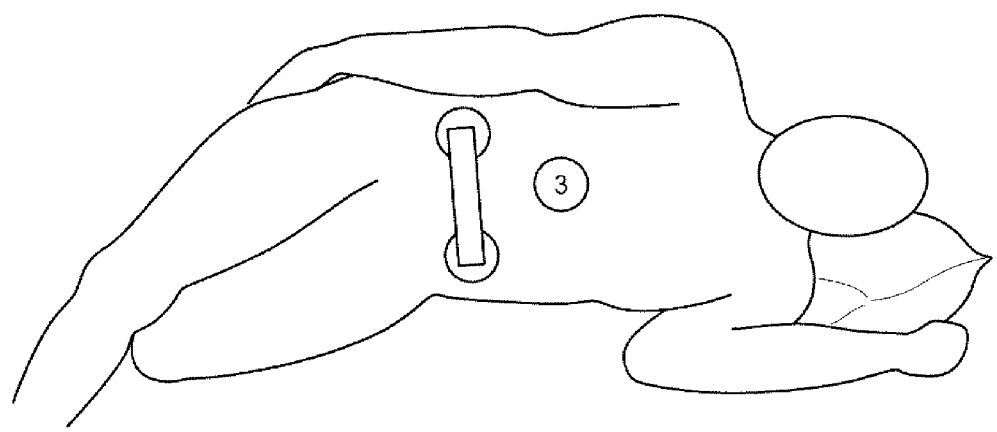
FIG. 4 is a schematic view of the patient with the colonoscopy abdominal compression device of FIGS. 1 and 2 in position.

In FIG. 3, a patient has abdominal sites marked with the arrows shown. These are the major points of contact for abdominal pressure. Once the patient is sedated, point number one in the lower left quadrant is located and device 10 as shown in FIG. 4 is located with the pressure columns held to sites one and two. The patient is positioned left lateral with the inferior leg at a straight position and the right leg slightly bent at the knee.

Figure 5:
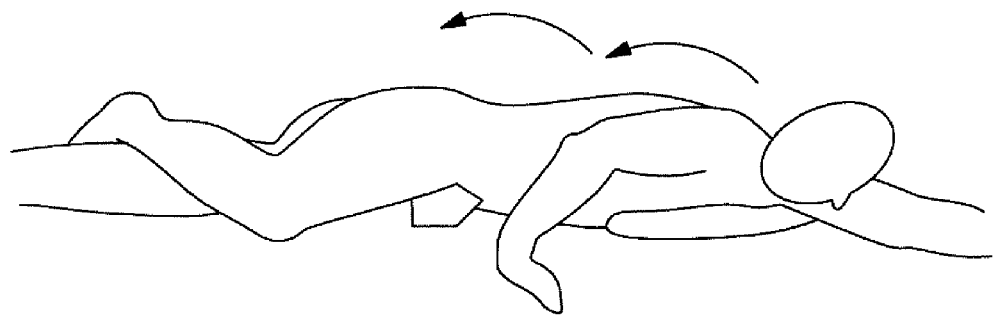
FIG. 5 is a schematic view of the patient now in a prone position.
Figure 6:
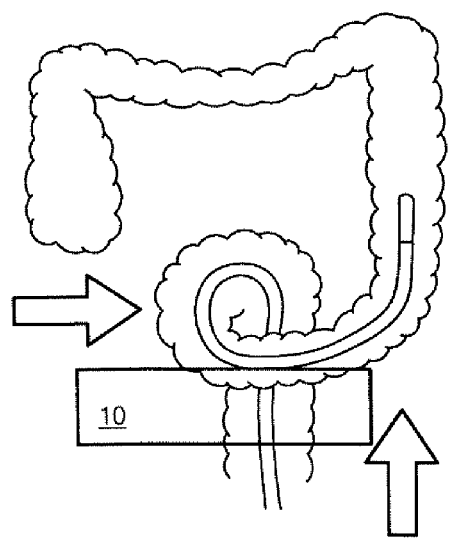
FIG. 6 is a schematic view showing the compression device of FIGS. 1 and 2 against a patient's pelvis.
Figure 7:
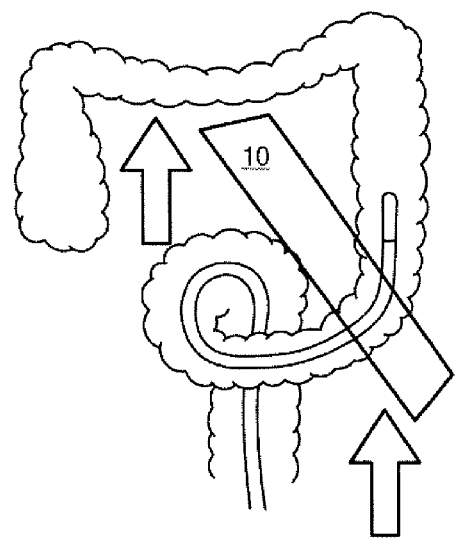
FIG. 7 is a schematic view showing the compression device of FIGS. 1 and 2 oriented against a patient's iliac and epigastic regions.

Next, the lower hip contact point is shifted so the center of gravity is toward prone and the patient is rolled toward prone so that the inferior pressure column is contacted with the first marked point, the lower left quadrant. The superior column here has minor contact with the abdomen. The column of point number one is the main pressure point at this time as shown in FIG. 5. The colonoscopy then begins and the nurse's hand can be gently placed beneath the palpation arch to monitor scope movement and for loop control. If the loop is more medial, the point of contact of the pressure column can be adjusted. If looping is also originating to the right lower quadrant, the patient can be rolled full prone with the device in place so that both pressure columns press on the iliac. The most common loop formed is the alpha loop. Positioning of the device as shown in FIG. 6 will control the majority of loops. The arrows indicate the vector of compression. In FIG. 7 the device is oriented differently. Once the tip of the scope is in the hepatic flexure region, transverse looping may need to be controlled. This can be accomplished by turning the device as shown in FIG. 7 so that the new contact points are inferior to superior at pressure points one and three. Again, the arrows indicate vectors of compression.

Figure 8:
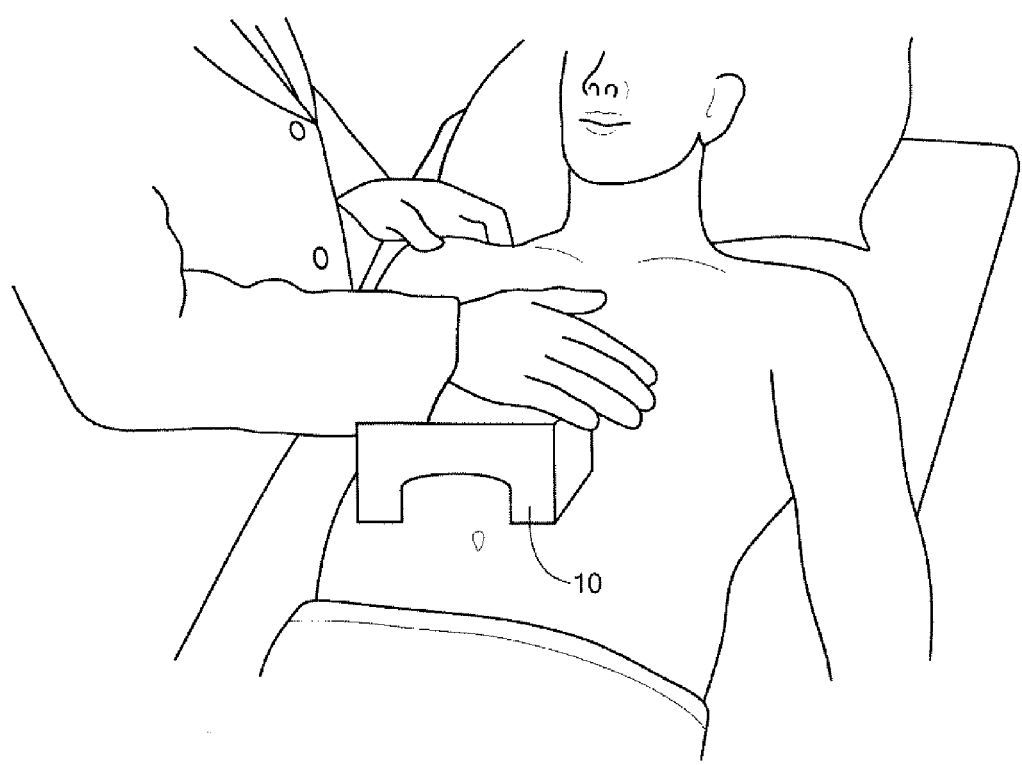
FIG. 8 is a schematic view of a nurse applying pressure to the palpation bridge of the patient colonoscopy abdominal compression device of FIGS. 1 and 2.

Advancing to the ascending colon is by an accommodation of maneuvers occurring simultaneously. With the device in place with the last successful contact points, the patient may be asked to take a deep breath and hold while the endoscope advances and the patient rolls prone. In the event the patient position needs to be changed to supine, it is determined where pressure is to be applied. The device as shown in FIG. 8 is then placed at this location and the nurse rests his forearms on the fulcrum edge and leans into the patient so the nurse's body weight does the actual loop control. Again, the palpation arch can be used to determine repositioning necessity.

Although specific features of the vention are shown in some drawings and not in others, this is for convenience only as each feature may be combined with any or all of the other features in accordance with the invention. The words "including", "comprising", "having", and "with" as used herein are to be interpreted broadly and comprehensively and are not limited to any physical interconnection. Moreover, any embodiments disclosed in the subject application are not to be taken as the only possible embodiments.

In addition, any amendment presented during the prosecution of the patent application for this patent is not a disclaimer of any claim element presented in the application as filed: those skilled in the art cannot reasonably be expected to draft a claim that would literally encompass all possible equivalents, many equivalents will be unforeseeable at the time of the amendment and are beyond a fair interpretation of what is to be surrendered (if anything), the rationale underlying the amendment may bear no more than a tangential relation to many equivalents, and/or there are many other reasons the applicant can not be expected to describe certain insubstantial substitutes for any claim element amended.

Other embodiments will occur to those skilled in the art and are within the following claims.

What is claimed is:

1. A patient colonoscopy abdominal compression device comprising:
    spaced rectangular pressure columns each having an end portion which tapers to a flat, square-shaped face area configured to press on a patient's iliac region;
    an arch between the spaced pressure columns configured to allow a hand to pass between the spaced pressure columns for monitoring scope movement and loop control; and
    a top surface including a flat arch face with corner edges configured to serve as fulcrum points for pivoting the device and to transfer pressure from the patient or a nurse to the patient's iliac region via the spaced pressure columns.

2. The device of claim 1 in which, before the taper, the pressure columns are rectangular in cross section.

3. The device of claim 1 in which there are two spaced pressure columns.

4. The device of claim 1 in which the arch is curved.

5. The device of claim 1 in which the pressure columns and arch are made of closed cell foam.

6. The device of claim 1 in which, before the taper, the spaced pressure columns are square in cross section.

7. A patient colonoscopy abdominal compression device comprising:
    first and second spaced pressure columns each 5 inches long and configured to press on a patient's iliac region, each pressure column tapering to a pressure face which is 1 inch long and 1 inch wide; and
    a curved arch which is 2¾ inches thick and 2 inches wide between the spaced pressure columns, the curved arch configured to allow a hand to pass between the spaced pressure columns for monitoring scope movement and loop control, and further configured to transfer pressure from the patient or a nurse to the iliac region via the pressure columns, the arch also including a top surface 8 inches long and 2 inches wide with spaced fulcrum edges for pivoting the device.

8. The device of claim 7 in which, before the taper, the first and second spaced pressure columns are square in cross section.

9. The device of claim 7 in which the first and second spaced pressure columns and the curved arch are made of closed cell foam.

* * * * *